(12) United States Patent
Volker

(10) Patent No.: US 8,789,558 B2
(45) Date of Patent: Jul. 29, 2014

(54) FLUID SYSTEM FOR SUPPLYING A DEVICE WITH HIGHLY PURE LIQUID

(76) Inventor: Manfred Volker, Blankenbach (DE)

( * ) Notice: Subject to any disclaimer, the term of this patent is extended or adjusted under 35 U.S.C. 154(b) by 45 days.

(21) Appl. No.: 13/581,559

(22) PCT Filed: Feb. 22, 2011

(86) PCT No.: PCT/DE2011/000167
§ 371 (c)(1),
(2), (4) Date: Aug. 28, 2012

(87) PCT Pub. No.: WO2011/107069
PCT Pub. Date: Sep. 9, 2011

(65) Prior Publication Data
US 2012/0325351 A1 Dec. 27, 2012

(30) Foreign Application Priority Data
Mar. 2, 2010 (DE) .......... 10 2010 009 816

(51) Int. Cl.
*F17D 3/00* (2006.01)
(52) U.S. Cl.
USPC ............ 137/599.01; 251/149.6; 138/111; 210/232
(58) Field of Classification Search
CPC .... A61M 1/16; A61M 1/1654; A61M 1/1656
USPC .......... 137/597, 599.01; 138/111; 251/149.6; 210/232, 252, 321.6, 321.71
See application file for complete search history.

(56) References Cited

U.S. PATENT DOCUMENTS

| 3,809,241 | A * | 5/1974 | Alvine .......................... 210/87 |
| 6,235,199 | B1 * | 5/2001 | Peterson et al. ............. 210/646 |
| 6,319,399 | B1 * | 11/2001 | Peterson et al. ............. 210/232 |
| 6,537,450 | B2 * | 3/2003 | Russell et al. ................ 210/194 |
| 7,252,652 | B2 * | 8/2007 | Moorehead et al. .......... 604/247 |
| 8,425,767 | B2 * | 4/2013 | Fava et al. ....................... 210/86 |
| 8,549,936 | B2 * | 10/2013 | Volker ...................... 73/864.15 |
| 2012/0167997 | A1 * | 7/2012 | Brensing et al. ................ 137/14 |
| 2012/0279492 | A1 * | 11/2012 | Spinelli et al. ................ 126/663 |

FOREIGN PATENT DOCUMENTS

| DE | 19520916 A1 | 1/1997 |
| DE | 19528160 A1 | 1/1997 |
| DE | 10256584 | 5/2004 |
| DE | 102007018595 B3 | 7/2008 |
| DE | 102008013109 A1 | 9/2009 |

OTHER PUBLICATIONS

International Search Report from the European Patent Office, mailed Jul. 22, 2011.

* cited by examiner

*Primary Examiner* — John Rivell
*Assistant Examiner* — Reinaldo Sanchez-Medina
(74) *Attorney, Agent, or Firm* — Greer, Burns & Crain, Ltd.

(57) ABSTRACT

The fluid system for supplying a dialysis device with permeate has a secondary ring line which is guided within a common insulating hose or another form-fit sheathing. Thus, heat loss is reduced and use is facilitated. The insulating hose having the inner lines is adapted to a flow-optimized coupling handpiece having low dead space, which can preferably be coupled to a mating coupling piece.

11 Claims, 2 Drawing Sheets

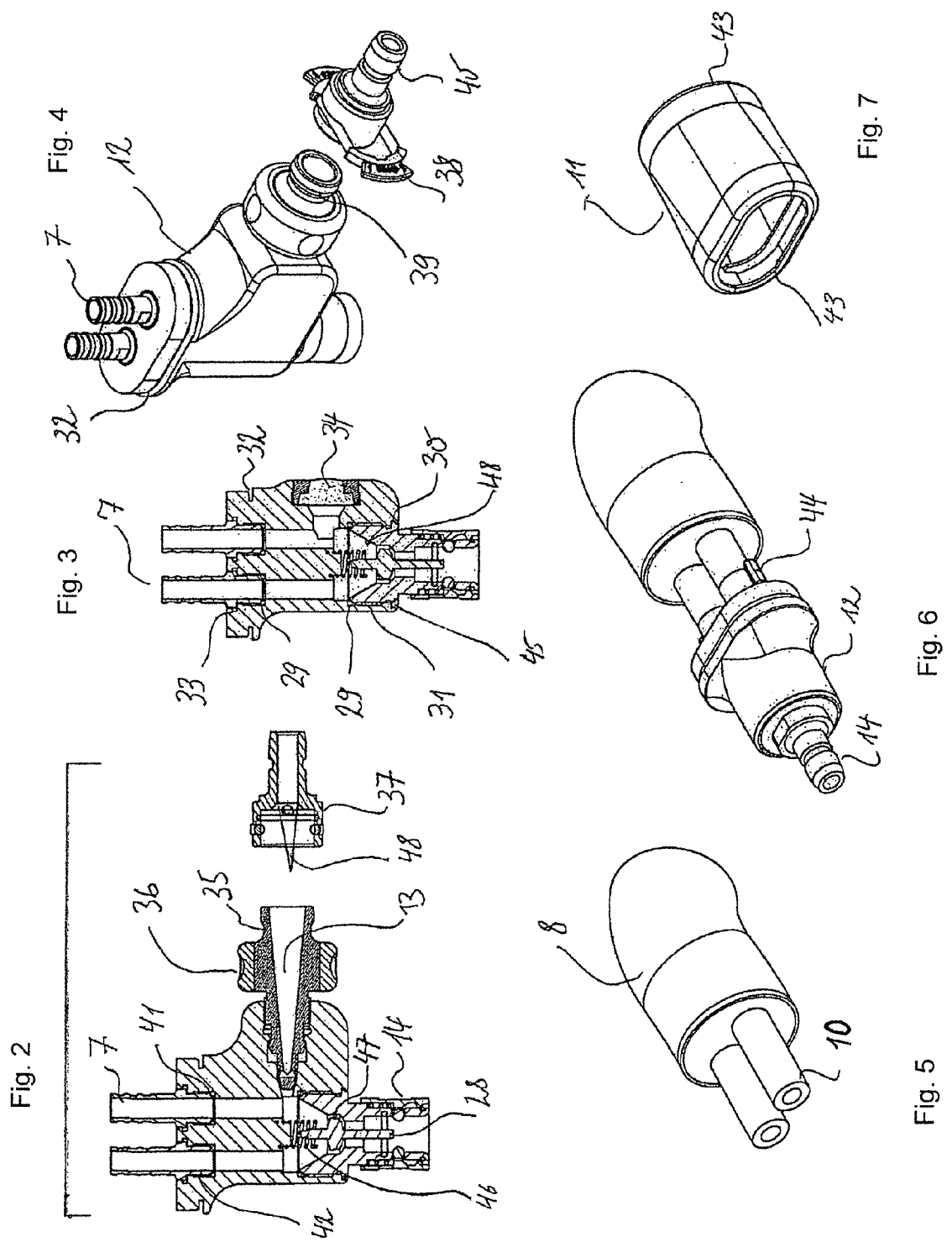

FLUID SYSTEM FOR SUPPLYING A DEVICE WITH HIGHLY PURE LIQUID

CROSS REFERENCE

This application is a U.S. National Phase under 35 U.S.C. §371 of International Application No. PCT/DE2011/000167, filed Feb. 22, 2011, which claims priority from German Patent Application No. 10 2010 009 816.7, filed Mar. 2, 2010.

FIELD OF THE INVENTION

The present invention refers to a fluid system for supplying a device, particularly a dialysis device, with ultrapure liquid, particularly permeate, comprising a liquid-conducting conduit from which a secondary line, particularly a secondary ring line, branches off and ultrapure liquid is supplied through said secondary ring line to the device.

This may be ultrapure liquid or a more or less ready-for-use dialysis liquid or a concentrate of said liquid that is used in the individual dialysis device by dilution with water and/or other constituents for preparing the dialysis liquid.

Devices of such types are suited in dialysis devices particularly for the supply with the water needed for preparing the dialysis liquid, and special demands have to be made on the purity and sterility thereof.

BACKGROUND

DE 195 20 916 A1 and DE 102 56 584 of the applicant and DE 2008 013 109 A2 already disclose devices in which the liquid is passed without stagnation to the dialysis devices.

DE 2008 013 109 A1 and DE 195 20 916 A1 show two main lines and loop-forming secondary lines branched off therefrom. Apart from the higher installations costs and the confusing hose routing a large amount of liquid must circulate so that enough liquid flows through all branches. As a consequence, the reverse osmosis or the circulating pump has to be designed with a much greater size to ensure overflow also during return.

As a consequence, one must expect an increased heating of the permeate and a microbial contamination risk resulting therefrom for osmosis and ring line.

Moreover, further drawbacks of this arrangement are the great flushing volume which is e.g. needed after a chemical disinfection so that toxic residues are avoided, as well as the temperature losses during hot cleaning that are caused by the larger surface of the distribution system.

Another serious drawback of all of these devices is that a coupling to a dialysis device without dead space or with low dead space is not possible.

Although the liquid circulates in the main and loop-forming branch lines, the liquid stagnates in the feed line within the dialysis device. Hence, colonization by germs may occur and there is the risk of recontamination of the main and loop-forming branch lines.

A further drawback is the handling of the branch or secondary ring line consisting of two hoses. It is only with great efforts that the high hygiene demand of a dialysis station can be satisfied with respect to the surface hygiene of the hoses which are partly also lying on the floor.

An essential drawback is the handling and the risk of burning at the arising high surface temperatures during hot cleaning, as well as the considerable heat loss in the environment.

In addition the connection to the dialysis device is not without dead spaces, so that even in the case of a circulating liquid within the loop-forming branch lines the coupling piece is not back-flushed. There is thus an increased risk of the colonization by germs and the propagation of germs, particularly in the coupling valve area, and of ensuing germ re-transportation into the main line.

Moreover, direct sampling for controlling the microbiological purity or the chemical composition of the liquid at the transfer point to the dialysis device has so far not been possible.

Moreover, the used coupling materials are of special steel, they are difficult to work on, they are expensive and have to be protected during hot cleaning against contact and heat loss.

SUMMARY OF THE INVENTION

It is the object of the present invention to design a device for supplying dialysis devices with ultrapure water in such a manner that a stagnation of the liquid is avoided and that a hygienic, simple handling at a low temperature loss is possible during hot cleaning.

According to the invention this object is achieved by a fluid system for supplying a device, particularly a dialysis device, with ultrapure liquid, particularly permeate, as more fully described herein below.

The invention provides a secondary ring line which is guided within a common insulating hose or another form-fit sheathing. This reduces heat losses and makes the use easier. The insulating hose with the two inner liquid-conducting lines is here adapted to a flow-optimized coupling handpiece (device connection block) having low dead space, which can preferably be coupled to a mating coupling piece which is fastened to the housing of the device or a permeate supply tank.

The coupling handpiece comprises a first hole which is connectable to the feed hose of the secondary ring line and a second hole which is connectable to the return hose of the secondary ring line, the holes terminating in one another and forming a tapering, preferably conical inlet in the hose connection block. Moreover, the hose connection block comprises a third hole which is connected to said preferably conical inlet and which preferably at the opposite side of the coupling handpiece has an outlet; the third hole or the conical inlet has arranged therein a preferably spring-loaded valve body which in the decoupled state of the hose connection block closes the third hole and is moved into the opening position in the state where it is assembled with the mating coupling. The valve is back-flushed in the conical inlet.

Furthermore, the invention provides that the third hole of the coupling handpiece in the coupling state is connected to the filling line of the device. In the filling line of the consumer a water inlet valve or permeate release valve is further arranged that can block or release the flow of the liquid.

With great advantage the invention provides a flushing valve which is connected in parallel with the permeate release valve for flushing or disinfecting the secondary ring line or the consumer filling line. To this end the consumer may be switched off. Furthermore, it is suggested that for the regulation of the flushing flow a constant-flow orifice should be inserted in the line of the flushing valve or in the flushing valve itself.

The outlet of the flushing valve may here be arranged inside the dialysis device or also outside e.g. in the media supply.

It is advantageous to control the flushing valve via the electronic system of the RO system and via a BUS connection, hard-wired or by means of radio transmission, for addressing the flushing valves. The control can also be carried out via the consumer or also in combination with RO system and consumer.

This accomplishes a coupling virtually without dead space and also a flushing or disinfection of the secondary ring line to the consumer, e.g. to the dialysis device.

The coupling handpiece is preferably made of plastic, so that the coupling can be produced at relatively low material costs. To protect the coupling against unintended twisting out of the hose connection block, it may be secured by means of a screw type locking connection.

With great advantage it may further be provided that a sample taking valve is fastened either to the coupling handpiece or to the consumer connection coupling and communicates with an associated hole of one of the two coupling members. A sample of the permeate can thus be taken in an easy way in the direct vicinity of the dialysis device.

With great advantage the sample taking valve contains a conically outwardly expanding hole from which the permeate taken flows off almost completely without permeate drops sticking to the walls of the hole. This substantially prevents contamination of the permeate during outflow from the sample taking valve. The hole can also be flame-cleaned prior to sample taking, whereby contamination of the sample is ruled out. A lockable adapter with Luer Lock connection is provided for transfer and accommodation of the sample.

As an alternative to the aforementioned conical sample-taking valve, it is also possible to insert a septum, as is e.g. used in pain therapy for medicament metering. The sample is here taken with a thin-walled, correspondingly ground syringe needle after the septum has been pierced.

The invention further provides that at least one connection block which comprises a main supply passage channel which forms a section of the main supply line is inserted into the main supply line, and that at an angle relative to the main supply passage channel, preferably at a right angle, a flow block is inserted into a hole of the connection block, comprising at least one secondary passage channel which is in fluid communication with the main supply passage channel and to which a secondary line is connectable on the outside of the flow block, and that the flow block comprises a flow resistance body which projects into the main supply passage channel and effects that fluid enters into the secondary passage channel. The flow resistance body is here made integral with the flow block.

One or two secondary passage channels may pass through the flow block, depending on whether a secondary branch line or a secondary ring line leads to the consumer.

In one embodiment, the secondary passage channel/the secondary passage channels extend through the flow resistance body, and a secondary passage channel which is formed upstream with respect to the flow in the main supply line and which extends preferably at a right angle to the main supply passage channel is in flow communication with the main supply passage channel through a hole branching off at a right angle. This hole or entry opening for the fluid is preferably positioned approximately in the center of the main supply passage channel.

When a second secondary passage channel is provided in this embodiment, it is positioned, viewed in flow direction, at a distance behind the first secondary passage channel and extends in parallel therewith. The second secondary passage channel is provided with a hole or exit opening branching off at a right angle, through which the fluid flowing back is again introduced into the main supply passage channel. In this embodiment the flow resistance body is an orifice which in cross section preferably has a semicircular form the straight boundary surface of which preferably extends in parallel with the longitudinal axis of the main supply passage channel. Other flow-promoting forms of the orifice are within the scope of the invention.

In another embodiment an orifice is provided as the flow resistance body, which in cross section has the profile of a wing that is arranged with its longitudinal extension in the longitudinal direction of the main supply passage channel in the main supply channel. In this embodiment the secondary passage channel/the secondary passage channels do not extend through the orifice, but end in the face of the flow block that is facing the main supply passage channel, with a secondary passage channel being arranged above the wing profile and the other secondary passage channel with its opening under the wing profile. Due to the pressure difference above and below the wing profile fluid flows through the secondary ring line.

It is within the scope of the invention that a connection block which is inserted into the main supply line may have integrated two or three flow blocks from which a respective secondary branch line or a secondary ring line branches off. An associated flow block is provided for each consumer, and it goes without saying that a plurality of connection blocks may also be inserted into the main supply line.

The flow block is inserted with a front section into the hole of the connection block, while a rear section of the flow block remains outside the connection block. Preferably, at least the inserted section has a circular form, when viewed in cross-section, and it is seated in a form-fit manner in the hole of the connection block. It is here preferred that the flow block is inserted into the hole. This facilitates assembly and possibly disassembly of the flow block, and the circular form of the hole enables the setting of the inclination angle of the flow resistance body. The face wall of the inserted section is preferably flat. The mounting of the connection block into the permeate supply line may be selected as a metal clamp or pipe connection and also as a plastic bead and groove-free weld-in part.

The present invention ensures a fluid system that avoids the known drawbacks and offers a high hygienic standard together with low investment and operating costs.

BRIEF DESCRIPTION OF THE DRAWINGS

FIG. 2 is a first sectional view of a device connection block.
FIG. 3 is a second sectional view of the device connection block.
FIG. 4 is a perspective view of the device connection block.
FIG. 5 is a perspective view of an end section of an insulating hose.
FIG. 6 is a perspective view of the end section of the insulating hose connected to the device connection block.
FIG. 7 is a perspective view of a strain relief collar.

DETAILED DESCRIPTION OF PREFERRED EMBODIMENT

Figure 1:
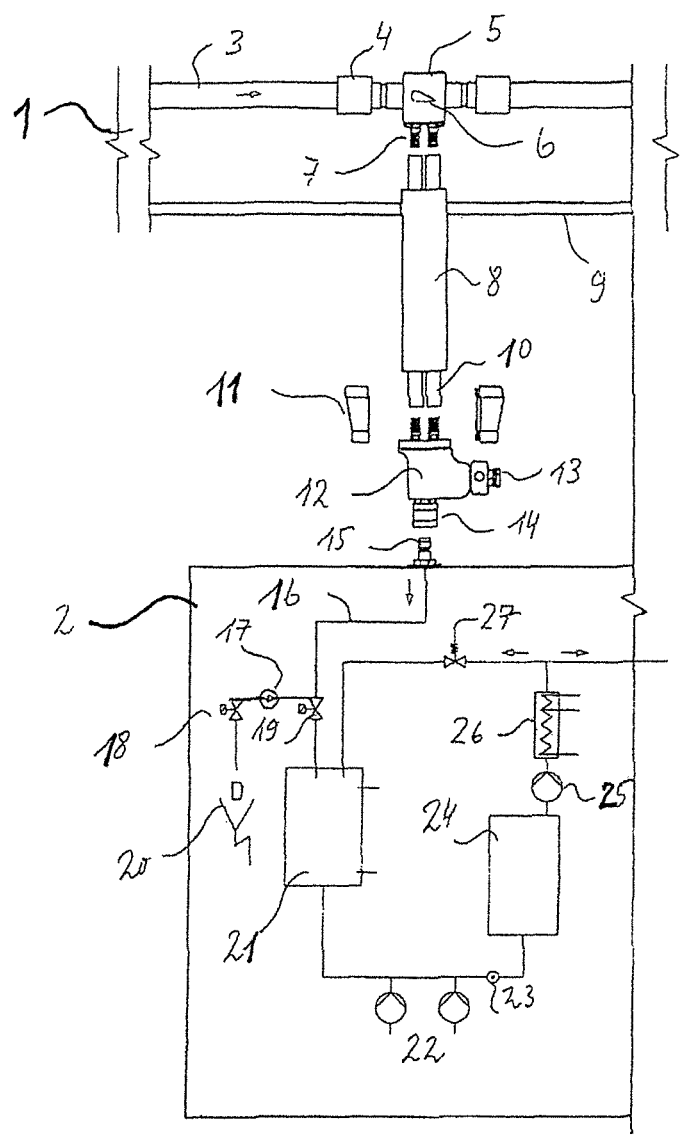
FIG. 1 is a schematic diagram of a fluid system.

Further details of the invention become apparent from the subsequent description of a few preferred embodiments and from the drawings, in which:

FIG. 1 shows the procedure of the invention. The part marked with 1 is the media supply; the part marked with 2 is the dialysis device. The permeate is passed through the conduit 3 to the ring-line connection block 5 (hereinafter called "RLB"). The ring line may here be connected by means of the press sleeve 14 or by a welding method. The interior of the RLB contains the flow body 6 which guides part of the permeate via the connections of the secondary ring line 7 and the inliner hoses 10 to the device connection block 12 (hereinafter called "GAB"). The strain relief shells 11 fix the insulating hoses 8 in the compressed state. In the opened state of the water inlet valve 19 a partial permeate stream is passed via the connection coupling 14 to the supply tank 21 of the dialysis device. During the flushing and cleaning cycle a defined permeate amount can be passed via the dialysis device inlet 16, the constant flow throttle 17 and the flushing valve 18 to the outlet 20. The outlet may here be arranged inside and outside the dialysis device. The GAB 12 can be equipped with a sample taking point 13.

FIGS. 2-4 is a sectional and perspective view, first of all showing the GAB 12. The connections of the secondary ring line 7 are here sealed via a seal slant 41 and seals 29. Fastening is carried out by means of latch 33 which is mounted as a collar on the connections 7 and engages into a groove of the GAB 12. Moreover, an additional fastening is carried out via thread 42. The rear edge of the GAB 12 has mounted thereon a holding groove 32 into which a collar 43 of the strain relief means 11 engages. This ensures a form-fit fastening of the strain relief means with the GAB 12 and the insulating hose 8. The collar 42 is formed on both ends of the strain relief means. The front side of the GAB 12 has mounted therein a coupling 14 with a thread fastening 31 and a coupling lock 30 the collar 45 of which engages into a groove of the GAB 12. This accomplishes a form-fit coupling assembly which is also loadable at high temperatures. The coupling is sealed at the rear end with a seal ring 29 by inclined pressing. The coupling is sealed by means of valve 28, spring 46 and sealing ring 47. The whole valve seat is back-flushed due to the V-shaped shape 48 of the coupling. A sample taking means 13 with a plastic or metal core 35 and an anti-contact sheath 36 is turned into the GAB. Sample taking is carried out via adapter 37 with coupling mandrel 49. The sample is passed on via an adapter connection 40 which may be configured as a Luer Lock or standard coupling. The sample taking adapter is fixed by means of a double lock 38 which in the fixed state engages into lock 39. As an alternative to the sample taking means 13, a plastic form septum 34 may be used. Instead of the coupling 14 a nipple configuration is also useable.

FIGS. 5-7 shows the end section of the insulating hose 8 with the inliner hoses 10, the connected state with the GAB 12 and the strain relief means 11.

It should be noted that the invention is not limited to the described and illustrated embodiments. Rather, all of the disclosed features of the embodiments can be combined with one another in any reasonable way also individually.

| | |
|---|---|
| 1. | RO media supply |
| 2. | Dialysis device DG |
| 3. | Permeate line |
| 4. | Clamp-, weld-in point or press sleeve |
| 5. | Ring-line connection block |
| 6. | Flow body |
| 7. | Connections for secondary ring line |
| 8. | Insulating hose or sheath |
| 9. | Front wall media supply |
| 10. | Secondary ring line inliner hoses |
| 11. | Strain relief |
| 12. | Device connection block |
| 13. | Sample taking |
| 14. | Connection coupling/nipple |
| 15. | DG connection coupling |
| 16. | DG inlet |
| 17. | Flow throttle |
| 18. | Drainage valve |
| 19. | DG filling valve |
| 20. | Outlet |
| 21. | Supply tank DG |
| 22. | Concentrate pumps |
| 23. | Degassing throttle |
| 24. | Degassing chamber |
| 25. | Circulation pump |
| 26. | Heater |
| 27. | Pressure holding valve |
| 28. | Coupling valve |
| 29. | Seal |
| 30. | Coupling lock |
| 31. | Coupling fastening thread |
| 32. | Holding groove strain relief |
| 33. | Locking secondary ring-line connections |
| 34. | Septum |
| 35. | Flame-cleaned core |
| 36. | Anti-contact sheath |
| 37. | Sampling taking adapter with coupling mandrel |
| 38. | Lock |
| 39. | Locking groove |
| 40. | Adapter connection (Luer Lock or coupling) |
| 41. | Sealing slant |
| 42. | Thread |
| 43. | Collar |
| 44. | Hose clip |
| 45. | Collar coupling latch |
| 46. | Coupling spring |
| 47. | Sealing ring |
| 48. | V-shaped coupling screw-in part with valve seal seat |

The invention claimed is:

1. A fluid system for supplying a device with ultrapure liquid comprising a liquid-conducting conduit from which a secondary line branches off, through which the ultrapure liquid is supplied to the device, wherein the conduit has installed therein a ring-line connection block, two inliner hoses are connected to the ring-line connection block and arranged in an insulating hose, the two inliner hoses are further connected to a device connection block to which a first coupling member with a valve seal seat is fastened, the device connection block has two holes connected to the two inliner hoses that terminate in an inlet from which a third hole extends which is led out of the coupling member, the third hole being closable by a valve body which is moved into the open position when a device connection coupling member is coupled to the first coupling member, the device connection coupling member being connected to the secondary line which supplies the device.

2. The fluid system according to claim 1, wherein the inlet tapers towards the third hole.

3. The fluid system according to claim 2, wherein the inlet is substantially conically tapered.

4. The fluid system according to claim 2, wherein the area of the valve in the inlet is constantly flushed.

5. The fluid system according to claim 1, wherein a sample taking valve is fastened to the device connection block or to the device connection coupling member which communicates with a bore of the device connection block or the device connection coupling member.

6. The fluid system according to claim 5, wherein the sample taking valve has a conically outwardly expanding hole.

7. The fluid system according to claim 1, wherein, the device connection block consists of plastic.

8. The fluid system according to claim 1, wherein, a filling valve is arranged in the feed line leading to a supply tank of the dialysis device.

9. The fluid system according to claim 8, wherein a drainage line with a drainage valve branches off in flow direction in front of the filling valve.

10. The fluid system according to claim 1, wherein the device is a diaysis device and the ultra pure liquid is permeate.

11. The fluid system according to claim 1, wherein the valve body is spring loaded.

* * * * *